(12) United States Patent
Kobayashi

(10) Patent No.: US 8,187,264 B2
(45) Date of Patent: May 29, 2012

(54) ELECTRODE NEEDLE DEVICE WITH TEMPERATURE SENSOR

(75) Inventor: Susumu Kobayashi, Tokyo (JP)

(73) Assignee: Kabushiki Kaisha Top, Tokyo (JP)

( * ) Notice: Subject to any disclaimer, the term of this patent is extended or adjusted under 35 U.S.C. 154(b) by 658 days.

(21) Appl. No.: 12/304,972

(22) PCT Filed: Jul. 28, 2006

(86) PCT No.: PCT/JP2006/314960
§ 371 (c)(1),
(2), (4) Date: Dec. 15, 2008

(87) PCT Pub. No.: WO2008/012911
PCT Pub. Date: Jan. 31, 2008

(65) Prior Publication Data
US 2009/0228004 A1     Sep. 10, 2009

(51) Int. Cl.
*A61B 18/18* (2006.01)
(52) U.S. Cl. .............. 606/40; 606/29; 606/41; 606/49
(58) Field of Classification Search .............. 606/44, 606/27–29, 32–35, 37–42, 45–52
See application file for complete search history.

(56) References Cited

U.S. PATENT DOCUMENTS

| | | |
|---|---|---|
| 4,411,266 A | 10/1983 | Cosman |
| 5,437,662 A | 8/1995 | Nardella |
| 5,672,174 A | 9/1997 | Gough et al. |
| 6,544,231 B1 * | 4/2003 | Palmer et al. ............ 604/165.01 |
| 2003/0093007 A1 * | 5/2003 | Wood ............................ 600/564 |
| 2005/0228374 A1 | 10/2005 | Desinger et al. |

FOREIGN PATENT DOCUMENTS

| | | |
|---|---|---|
| JP | 11-511988 A | 10/1999 |
| JP | 2005-527291 A | 9/2005 |
| WO | WO-97/06739 A2 | 2/1997 |
| WO | WO-01/70114 A1 | 9/2001 |
| WO | WO-03/099150 A2 | 12/2003 |

* cited by examiner

*Primary Examiner* — Nicholas Lucchesi
*Assistant Examiner* — Leah Stohr
(74) *Attorney, Agent, or Firm* — Birch, Stewart, Kolasch & Birch, LLP

(57) ABSTRACT

In a needle electrode device with a temperature sensor, having a hollow outer needle (1), which can be pierced into an affected area and is coated with an insulating layer (11) on an outer peripheral surface except at its distal end, and an inner needle (2), which is passed through the outer needle and has the temperature sensor (21) at its distal end, so that a high frequency current is supplied to the outer needle through the inner needle, and having a coupled tube (3) coupled to the rear end of the outer needle, so that the rear end (22) of the inner needle is inserted into the coupled tube in such a way as to be freely adjustable in its position in an axial direction, the position adjustment of the inner needle is provided with a simple operation. The coupled tube (3) is provided inside with a spring member (32) including a winding portion (32*a*) around the outer circumference of the rear end (22) of the inner needle (2) and a fixed portion (32*b*) fixed to the coupled tube (3). Moreover, the rear end (22) of the inner needle (2) can be moved in the axial direction by rotating the rear end (22) of the inner needle (2) in the opposite direction to a winding direction of the winding portion (32*a*).

14 Claims, 4 Drawing Sheets

ELECTRODE NEEDLE DEVICE WITH TEMPERATURE SENSOR

BACKGROUND OF THE INVENTION

1. Field of the Invention

The present invention relates to a needle electrode device with a temperature sensor for medical application, for use in performing high frequency thermocoagulation, ablation, or the like of an affected area by applying a high frequency current to the affected area.

2. Related Background Art

Conventionally, there is already known a needle electrode device for medical application, having a hollow outer needle, which can be pierced into an affected area and is coated with an insulating layer on an outer peripheral surface except at its distal end, and an inner needle to be inserted into the outer needle, so that a high frequency current is supplied to the outer needle through the inner needle in order to apply the high frequency current to an affected area from the distal end of the outer needle, which is not coated with the insulating layer. As this type of needle electrode device, there is disclosed a needle electrode device provided with a temperature sensor at the distal end of the inner needle, so that the temperature of the affected area can be obtained by the temperature sensor (Refer to, for example, U.S. Pat. No. 4,411,266).

The length of the outer needle varies according to the manufacturer, or even if the manufacturer is the same, it varies in some degree from one product to another. Therefore, in order to grasp the temperature of the affected area accurately, it is necessary to adjust the position of the temperature sensor in accordance with the length of the outer needle, in other words, necessary to adapt the inner needle having the temperature sensor at the distal end in such a way as to be freely adjustable in its position in an axial direction relative to the outer needle. Therefore, conventionally there is also known a needle electrode device provided with a coupled tube, which is coupled to the rear end of the outer needle, wherein the rear end of the inner needle is inserted into the coupled tube in such a way as to be freely adjustable in its position in the axial direction.

In this type of needle electrode device, radially threaded holes are formed in the surrounding wall of the coupled tube, locking screws screwed into the threaded holes are pushed against the outer peripheral surface of the rear end of the inner needle so that the rear end of the inner needle can be fixed. In this structure, however, there is a need to loosen and tighten screws each time when adjusting the position of the inner needle. Therefore, this type of needle electrode device has a problem of troublesome operation.

SUMMARY OF THE INVENTION

In view of the above problem, it is an object of the present invention to provide a needle electrode device with a temperature sensor superior in usability, which is adapted in such a way that the position of an inner needle can be adjusted with a simple operation.

In order to achieve the above object, the present invention provides a needle electrode device with a temperature sensor, having a hollow outer needle, which can be pierced into an affected area and is coated with an insulating layer on an outer peripheral surface except at its distal end, and an inner needle, which is inserted into the outer needle and has the temperature sensor at its distal end, so that a high frequency current is supplied to the outer needle through the inner needle, and having a coupled tube coupled to the rear end of the outer needle, so that the rear end of the inner needle is inserted into the coupled tube in such a way as to be freely adjustable in its position in an axial direction, wherein the coupled tube is provided inside with a spring member including a winding portion to be wound around the outer circumference of the rear end of the inner needle and a fixed portion fixed to the coupled tube, and wherein the rear end of the inner needle can be moved in the axial direction by rotating the rear end of the inner needle in the opposite direction to a winding direction of the winding portion.

According to the present invention, the rear end of the inner needle does not move relative to the coupled tube due to a frictional force applied between the winding portion of the spring member and the outer peripheral surface of the rear end of the inner needle on a steady basis. On the other hand, when the rear end of the inner needle is rotated in the opposite direction to the winding direction of the winding portion, an unwinding force is applied to the winding portion, which reduces the frictional force applied between the winding portion and the outer peripheral surface of the rear end of the inner needle. Therefore, it is possible to move the rear end of the inner needle in the axial direction relative to the coupled tube to adjust the position of the inner needle or the temperature sensor at the distal end of the inner needle in the axial direction relative to the outer needle. Moreover, when adjusting the position of the inner needle, there is no need to loosen and tighten screws as in the prior art, and therefore it becomes easy to operate.

Meanwhile, if the position is adjusted only by pushing and pulling the rear end of the inner needle in the axial direction, an excess force is apt to be used and it is hard to make a delicate position adjustment. Therefore, generally the delicate position adjustment is made through a combined control of pushing and pulling the rear end of the inner needle while rotating the same. In the present invention, the winding portion can be unwound by utilizing the rotation of the combined control and therefore the position of the inner needle can be adjusted by the very rational control, which provides improved usability.

A coil spring or a spiral spring can be used as the spring member. If the spring member is composed of the coil spring, the coil spring is formed into a spring having a reduced diameter portion and an expanded diameter portion with the reduced diameter portion used as the winding portion around the rear end of the inner needle and the expanded diameter portion used as the fixed portion to the coupled tube. If the spring member is composed of the spiral spring, a radial inner portion of the spiral spring is used as the winding portion around the rear end of the inner needle and a radial outer portion of the spiral spring is used as the fixed portion to the coupled tube.

A high frequency current flows into the inner needle. Therefore, if the temperature sensor is in contact with the inner needle, an output signal of the temperature sensor is mixed with high frequency noise and the temperature measurement accuracy is deteriorated. In this case, if the inner needle is hollow and provided with a cap at its distal end, with the temperature sensor attached to the inner surface of the cap and electrically isolated from the inner needle, the output signal of the temperature sensor is not mixed with high frequency noise and an accurate temperature measurement is achieved.

DETAILED DESCRIPTION OF THE PREFERRED EMBODIMENTS

The preferred embodiments of the present invention will now be described in detail hereinafter with reference to the accompanying drawings. FIG. 1, FIG. 2, FIG. 3, and FIG. 4 illustrate a longitudinal sectional view showing a first embodiment of a needle electrode device according to the present invention, a cross-sectional view taken along line II-II of FIG. 1, a longitudinal sectional view showing a second embodiment of a needle electrode device according to the present invention, and a cross-sectional view taken along line IV-IV of FIG. 3, respectively.

Figure 1:
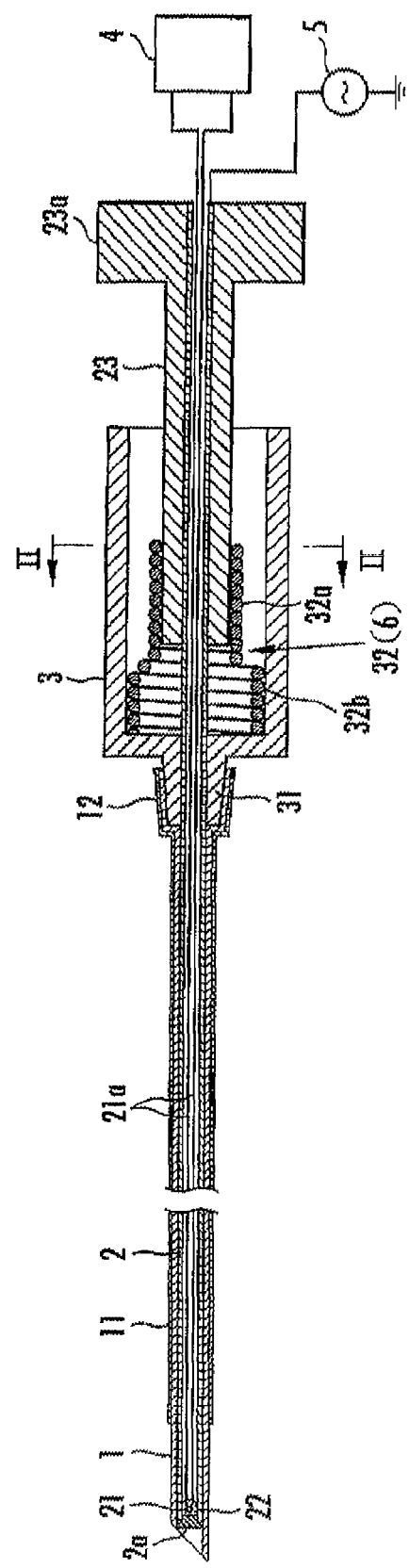
FIG. 1 is a longitudinal sectional view showing a first embodiment of the present invention.

Referring to FIG. 1, the needle electrode device of the first embodiment according to the present invention includes a hollow outer needle 1 made of metal, an inner needle 2 made of metal and inserted into the outer needle 1, and a coupled tube 3 made of resin and coupled to the rear end of the outer needle 1. The distal end of the outer needle 1 is sharply formed so that it can be pierced into an affected area. In addition, the outer needle 1 is coated with an insulating layer 11 on an outer peripheral surface except at its distal end. The outer needle 1 is detachably coupled to a luer taper 31 at the distal end of the coupled tube 3 with a hub 12 at the rear end of the outer needle 1.

The inner needle 2 is formed hollow. Furthermore, a temperature sensor 21 composed of a thermocouple is attached to the inner surface of a cap 2a put at the distal end of the inner needle 2 with being electrically isolated from the inner needle 2 by means of adhesive 22. Moreover, two wires 21a that continue into the temperature sensor 21 are inserted into the inner needle 2 and a temperature indictor 4 is connected to the wires 21a. In this way, a temperature detected by the temperature sensor 21 can be displayed on the temperature indicator 4. The inner needle 2 is filled with insulating material such as magnesium oxide. In addition, the inner needle 2 is connected to a high frequency power source 5. The inner needle 2 is then brought into contact with at least a part of the inner peripheral surface of the outer needle 1, so that a high frequency current is supplied to the outer needle 1 through the inner needle 2. Thus, the high frequency current flows from the distal end of the outer needle 1, which is not coated with the insulating layer 11, to the affected area into which the outer needle 1 is pierced, by which treatment such as high frequency thermocoagulation or ablation is given to the affected area.

Even if the high frequency current flows into the inner needle 2, the output signal of the temperature sensor 21 is not contaminated with high frequency noise and an accurate temperature can be measured since the temperature sensor 21 is attached to the inner needle 2 with being electrically isolated from the inner needle 2 as described above.

The rear end of the inner needle 2 is composed of a sleeve 23 fit and fixed onto the main body of the inner needle 2, which is inserted into the coupled tube 3. A knob 23a having a large diameter is formed at the rear end of the sleeve 23 exposed on the caudal side of the coupled tube 3. In addition, the coupled tube 3 is provided inside with a spring member 32 having a winding portion 32a wound around the outer circumference of the sleeve 23 and a fixed portion 32b fixed to the coupled tube 3. In this embodiment, the spring member 32 is composed of a coil spring 6 having a reduced diameter portion where the coil inner diameter is substantially equal to the outer diameter of the sleeve 23 and an expanded diameter portion where the coil outer diameter is substantially equal to the inner diameter of the coupled tube 3, with the reduced diameter portion used as the winding portion 32a around the sleeve 23. Furthermore, the expanded diameter portion 6b is used as the fixed portion 32b to the coupled tube 3 with being fixed to the inner peripheral surface of the coupled tube 3 by high frequency induction heating or the like. The coil spring 6 is formed in such a way as to leave no axial gap.

Figure 2:
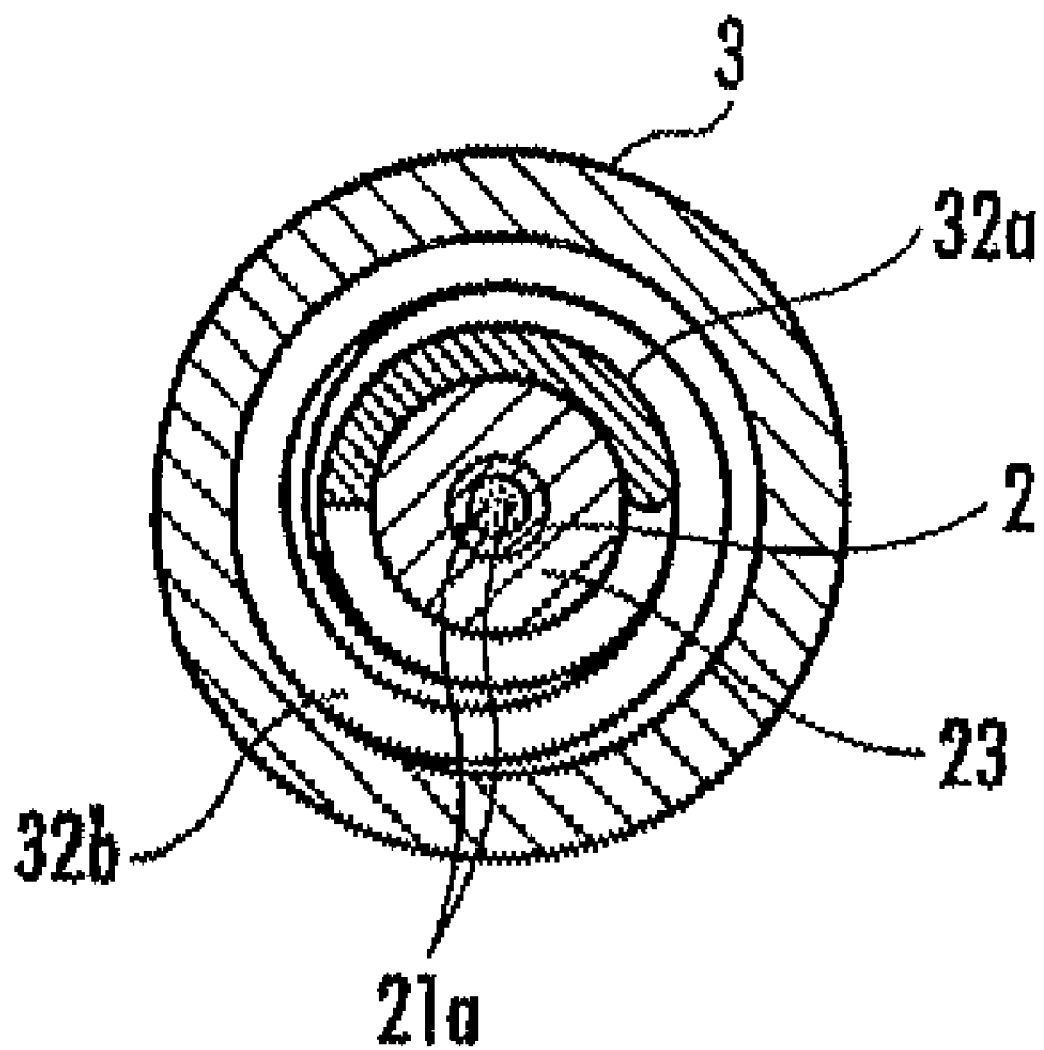
FIG. 2 is a cross-sectional view taken along line II-II of FIG. 1.

Note here that the winding direction of the winding portion 32a is counterclockwise when viewed from the axial caudal side as shown in FIG. 2. The sleeve 23 does not move relative to the coupled tube 3 due to the frictional force applied between the winding portion 32a and the outer peripheral surface of the sleeve 23 on a steady basis. On the other hand, when the sleeve 23 is rotated in the clockwise direction by grasping the knob 23a in FIG. 2, a force of unwinding the winding portion 32a is applied to the winding portion 32a, which reduces the frictional force applied between the winding portion 32a and the outer peripheral surface of the sleeve 23. Therefore, it becomes possible to adjust the position of the inner needle 2 or the temperature sensor 21 at its distal end in the axial direction relative to the outer needle 1 by moving the sleeve 23 in the axial direction relative to the coupled tube 3. Thereby, even if the length of the outer needle 1 varies in some degree, the temperature of the affected area can be accurately measured with the temperature sensor 21 placed in the optimal position on the needle point side of the outer needle 1.

Meanwhile, if the position is adjusted only by pushing and pulling the sleeve 23 in the axial direction, an excess force is apt to be used and it is difficult to make a delicate position adjustment. Therefore, generally the delicate position adjustment is made through a combined control of pushing and pulling the sleeve 23 while rotating it. In this embodiment, the position of the inner needle 2 (the temperature sensor 21) is adjusted by a very rational combined control such as pushing and pulling the sleeve 23 in the axial direction while rotating it in the clockwise direction, which provides improved usability.

Figure 3:
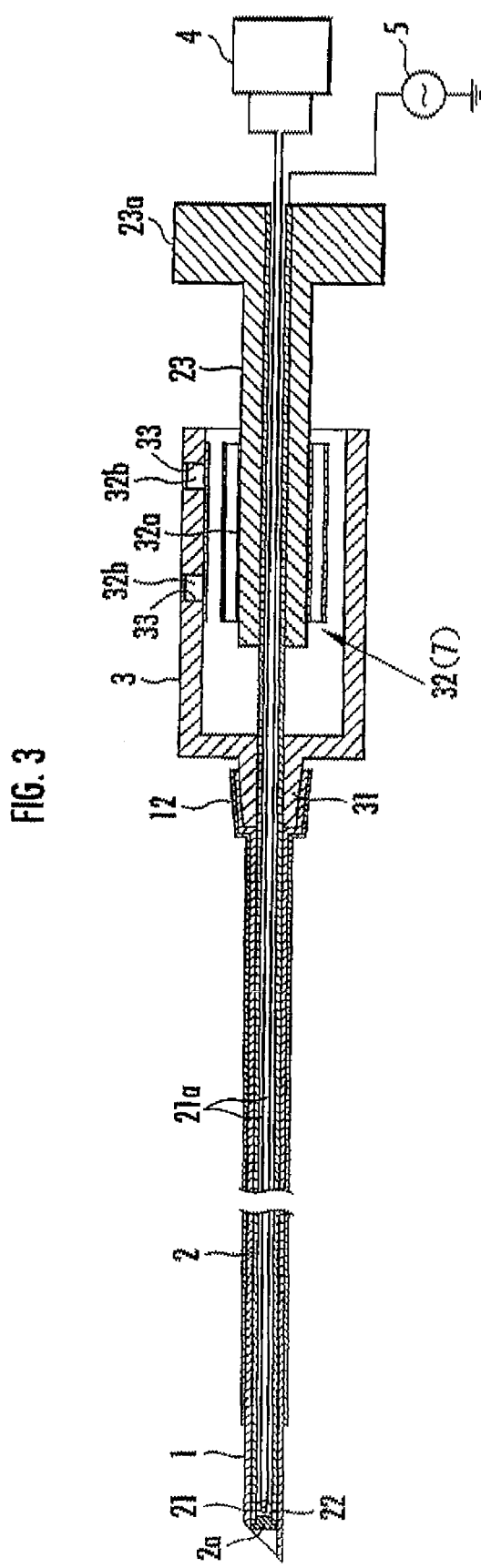
FIG. 3 is a longitudinal sectional view showing a second embodiment of the present invention.

Subsequently, a needle electrode device according to a second embodiment of the present invention will be described with reference to FIG. 3 and FIG. 4. The same components in the second embodiment as in the first embodiment described above are denoted by the same reference numerals as in the above. The second embodiment differs from the first embodiment in that a spiral spring 7 is used as the spring member 32. In this embodiment, the radial inner portion of the spiral spring 7 is the winding portion 32a around the sleeve 23. Furthermore, there is formed a detent projection, which engages with an engaging hole 33 formed in a surrounding wall of the coupled tube 3, in the radial outer portion of the spiral spring 7 and the detent projection is used as the fixed portion 32b to the coupled tube 3. Alternatively, the radial outer portion of the spiral spring 7 can be fixed to the coupled tube 3 by the high frequency induction heating or the like, so that the portion is used as the fixed portion 32b to the coupled tube 3.

Figure 4:
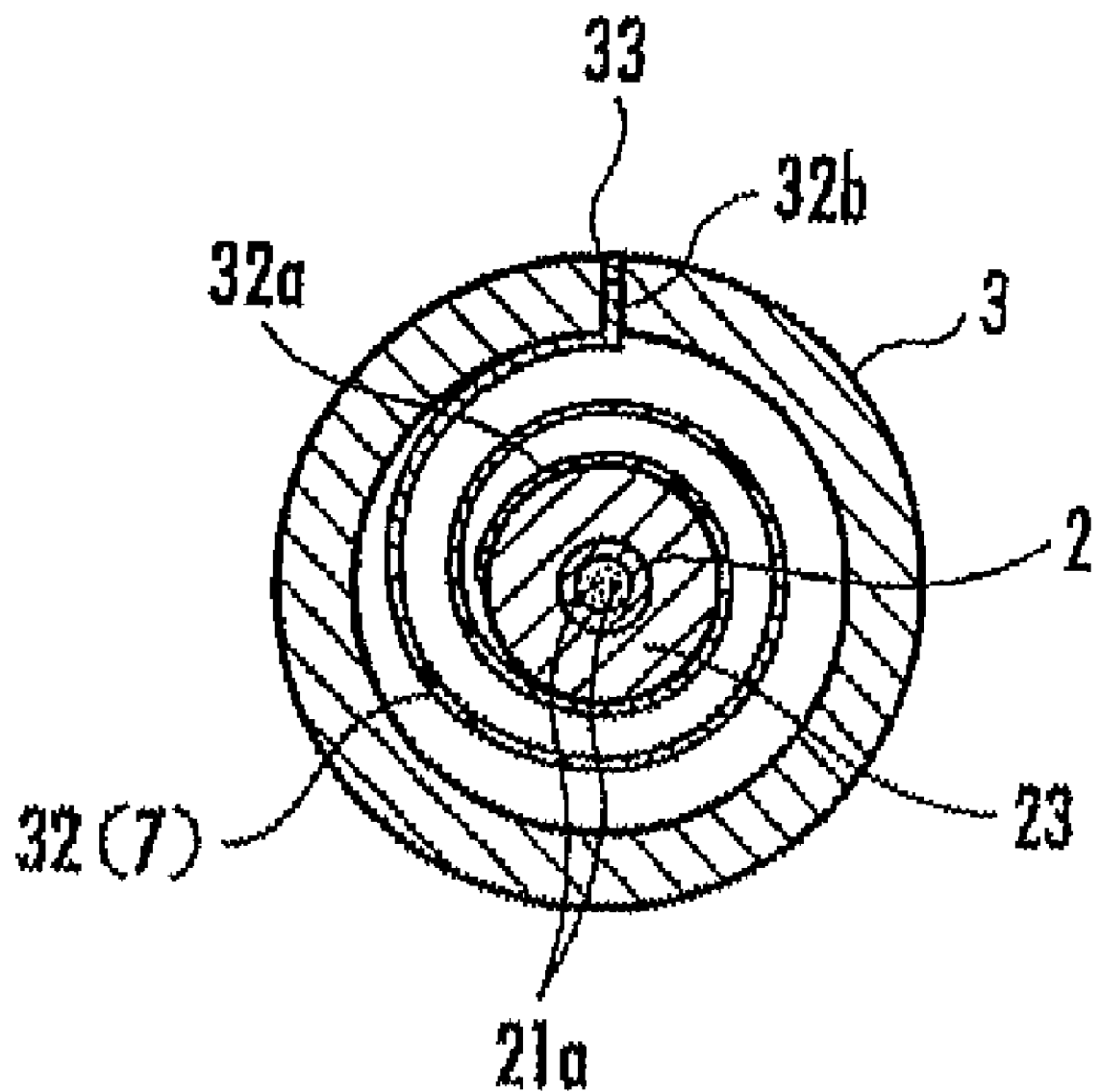
FIG. 4 is a cross-sectional view taken along line IV-IV of FIG. 3.

The winding direction of the winding portion 32a is counterclockwise when viewed from the axial caudal side as shown in FIG. 4. Therefore, when the sleeve 23 is rotated in the clockwise direction in FIG. 4, a force of unwinding the winding portion 32a is applied to the winding portion 32a. Thereby, in the same manner as in the first embodiment, it is possible to adjust the position of the inner needle 2 (the temperature sensor 21) in the axial direction relative to the outer needle 1 by moving the sleeve 23 in the axial direction relative to the coupled tube 3.

While the preferred embodiments of the present invention have been described hereinabove with reference to the accompanying drawings, it is to be understood that the subject matter encompassed by the present invention is not limited to those specific embodiments. For example, although the outer peripheral surface of the sleeve 23 is formed into a cylindrical surface in the above embodiments, a projection extending in the direction of the generatrix can be formed on the outer peripheral surface of the sleeve 23. According to this, the projection engages with an edge of the winding portion 32a when the sleeve 23 is rotated in the opposite direction to the winding direction of the winding portion 32a, by which a force of unwinding the winding portion 32a is efficiently transmitted to the winding portion 32a. In addition, while the thermocouple is used as the temperature sensor 21 in the above embodiments, it is also possible to use a thermistor or other temperature sensors besides the thermocouple.

What is claimed is:

1. A needle electrode device with a temperature sensor, having a hollow outer needle, which can be pierced into an affected area and is coated with an insulating layer on an outer peripheral surface except at its distal end, and an inner needle, which is inserted into the outer needle and has the temperature sensor at its distal end, so that a high frequency current is supplied to the outer needle through the inner needle, and having a coupled tube coupled to a rear end of the outer needle, so that a rear end of the inner needle is inserted into the coupled tube in such a way as to be freely adjustable in its position in an axial direction, wherein:
   the coupled tube is provided inside with a spring member including a winding portion to be wound around an outer circumference of the rear end of the inner needle and a fixed portion fixed to the coupled tube;
   the spring member is composed of a spiral spring, a radial inner portion of the spiral spring being used as the winding portion and a radial outer portion thereof being used as the fixed portion; and
   the rear end of the inner needle can be moved in the axial direction by rotating the rear end of the inner needle in the opposite direction to a winding direction of the winding portion.

2. The needle electrode device with a temperature sensor according to claim 1, wherein the inner needle is hollow and provided with a cap at its distal end, with the temperature sensor attached to the inner surface of the cap and electrically isolated from the inner needle.

3. The needle electrode device with a temperature sensor according to claim 1, wherein the spiral spring is secured to the coupled tube by a detent projection.

4. The needle electrode device with a temperature sensor according to claim 1, wherein the spiral spring is secured to the coupled tube by induction heating.

5. The needle electrode device with a temperature sensor according to claim 1, wherein the winding direction of the winding portion is counterclockwise wherein a fore of unwinding the winding portion in a clockwise direction enables an adjustment of the inner needle in the axial direction relative to the coupled tube.

6. The needle electrode device with a temperature sensor according to claim 1, wherein the temperature sensor is a thermocouple.

7. The needle electrode device with a temperature sensor according to claim 1, wherein the temperature sensor is a thermistor.

8. A needle electrode device with a temperature sensor comprising:
   a hollow outer needle coated with an insulating layer on an outer peripheral surface except at its distal end;
   an inner needle inserted into the outer needle;
   the temperature sensor being operatively positioned at a distal end of the inner needle;
   a coupled tube coupled to a rear end of the outer needle wherein a rear end of the inner needle is inserted into the coupled tube for freely adjusting a position of the inner needed in an axial direction;
   a spring member being disposed within the coupled tube, said spring member including a winding portion wounded around an outer circumference of the rear end of the inner needle and a fixed portion fixed to the coupled tube;
   said spring member being a spiral spring, a radial inner portion of the spiral spring being used as the winding portion and a radial outer portion thereof being used as the fixed portion;
   wherein the rear end of the inner needle is movable in the axial direction by rotating the rear end of the inner needle in the opposite direction to a winding direction of the winding portion.

9. The needle electrode device with a temperature sensor according to claim 8, wherein the inner needle is hollow and provided with a cap at its distal end, with the temperature sensor attached to the inner surface of the cap and electrically isolated from the inner needle.

10. The needle electrode device with a temperature sensor according to claim 8, wherein the spiral spring is secured to the coupled tube by a detent projection.

11. The needle electrode device with a temperature sensor according to claim 8, wherein the spiral spring is secured to the coupled tube by induction heating.

12. The needle electrode device with a temperature sensor according to claim 8, wherein the winding direction of the winding portion is counterclockwise wherein a fore of unwinding the winding portion in a clockwise direction enables an adjustment of the inner needle in the axial direction relative to the coupled tube.

13. The needle electrode device with a temperature sensor according to claim 8, wherein the temperature sensor is a thermocouple.

14. The needle electrode device with a temperature sensor according to claim 8, wherein the temperature sensor is a thermistor.

* * * * *